United States Patent
Rossodivito et al.

(10) Patent No.: US 11,517,734 B2
(45) Date of Patent: Dec. 6, 2022

(54) SYSTEM AND METHOD FOR DETECTING AIR EMBOLISMS IN LINES FOR HEMODYNAMIC MONITORING

(71) Applicants: Kristin Rossodivito, Valencia, CA (US); Cassondra Serrao, Simi Valley, CA (US)

(72) Inventors: Kristin Rossodivito, Valencia, CA (US); Cassondra Serrao, Simi Valley, CA (US)

( * ) Notice: Subject to any disclaimer, the term of this patent is extended or adjusted under 35 U.S.C. 154(b) by 1100 days.

(21) Appl. No.: 15/993,594

(22) Filed: May 31, 2018

(65) Prior Publication Data

US 2018/0369564 A1    Dec. 27, 2018

Related U.S. Application Data

(60) Provisional application No. 62/522,798, filed on Jun. 21, 2017.

(51) Int. Cl.
| | |
|---|---|
| *A61M 39/28* | (2006.01) |
| *A61B 5/0215* | (2006.01) |
| *A61B 5/026* | (2006.01) |
| *A61B 5/145* | (2006.01) |
| *A61M 25/00* | (2006.01) |
| *A61M 5/36* | (2006.01) |
| *A61M 5/168* | (2006.01) |

(52) U.S. Cl.
CPC .......... *A61M 39/281* (2013.01); *A61B 5/026* (2013.01); *A61B 5/0215* (2013.01); *A61B 5/14542* (2013.01); *A61M 5/16831* (2013.01); *A61M 5/365* (2013.01); *A61M 25/00* (2013.01); *A61B 2560/0266* (2013.01); *A61M 2025/0003* (2013.01); *A61M 2205/18* (2013.01); *A61M 2205/3306* (2013.01); *A61M 2205/3331* (2013.01); *A61M 2205/3368* (2013.01); *A61M 2205/3375* (2013.01)

(58) Field of Classification Search
None
See application file for complete search history.

(56) References Cited

U.S. PATENT DOCUMENTS

| | | | |
|---|---|---|---|
| 3,812,482 A | | 5/1974 | Clark |
| 3,834,372 A | * | 9/1974 | Turney ................ F16K 11/085 600/561 |
| 3,974,681 A | | 8/1976 | Namery |
| 4,112,773 A | * | 9/1978 | Abts ..................... G01N 29/032 73/61.79 |
| 4,397,335 A | * | 8/1983 | Doblar ................ A61M 39/223 604/32 |
| 4,428,383 A | * | 1/1984 | DeVroom ............ A61B 5/0215 600/561 |
| 4,625,494 A | * | 12/1986 | Iwatschenko ........ G05D 11/133 604/82 |
| 4,838,856 A | * | 6/1989 | Mulreany ......... A61M 5/16827 128/DIG. 13 |

(Continued)

*Primary Examiner* — Michael R Bloch
(74) *Attorney, Agent, or Firm* — Lincoln Law School of San Jose

(57) ABSTRACT

A system and method are provided for detecting air embolisms in lines for hemodynamic monitoring. In use, using a first sensor, one or more gas bubbles are detected within a first line for hemodynamic monitoring. In response to the detecting, a first clamp attached to the first line for hemodynamic monitoring is contracted.

11 Claims, 6 Drawing Sheets

(56) References Cited

U.S. PATENT DOCUMENTS

| | | | | |
|---|---|---|---|---|
| 4,884,065 A * | 11/1989 | Crouse | A61M 5/365 | 250/573 |
| 5,177,993 A * | 1/1993 | Beckman | A61M 5/14228 | 73/19.1 |
| 5,205,153 A * | 4/1993 | Hlavinka | G01N 29/223 | 73/64.53 |
| 5,382,232 A * | 1/1995 | Hague | A61M 5/365 | 128/DIG. 13 |
| 5,723,773 A * | 3/1998 | Bryan | G01N 29/032 | 73/19.1 |
| 5,840,058 A * | 11/1998 | Ammann | A61M 5/365 | 604/131 |
| 6,558,346 B1 * | 5/2003 | Yoshioka | A61M 5/1483 | 604/141 |
| 6,579,257 B1 * | 6/2003 | Elgas | A61M 1/3667 | 604/67 |
| 9,816,966 B2 * | 11/2017 | Sagebiel | G01N 29/032 | |
| 2003/0176833 A1 * | 9/2003 | Libermann | A61M 1/777 | 604/65 |
| 2006/0188407 A1 * | 8/2006 | Gable | A61B 5/0084 | 604/19 |
| 2008/0134750 A1 * | 6/2008 | Riley | A61M 5/365 | 73/19.03 |
| 2008/0208101 A1 * | 8/2008 | Boris-Moller | A61M 1/3627 | 604/4.01 |
| 2010/0234698 A1 * | 9/2010 | Manstrom | A61B 5/0215 | 600/301 |
| 2011/0239733 A1 * | 10/2011 | Sagebiel | G01N 29/222 | 73/19.03 |
| 2012/0101437 A1 * | 4/2012 | Gagliardoni | A61M 39/284 | 604/151 |
| 2013/0091953 A1 * | 4/2013 | Brown | A61M 5/365 | 73/642 |
| 2013/0317837 A1 * | 11/2013 | Ballantyne | A61M 1/3627 | 705/2 |
| 2015/0033823 A1 * | 2/2015 | Blumberg, Jr. | G01N 22/00 | 73/19.03 |
| 2016/0000366 A1 * | 1/2016 | Jensen | A61M 39/10 | 600/561 |
| 2016/0317762 A1 * | 11/2016 | Kimm | A61M 5/5086 | |
| 2016/0361484 A1 * | 12/2016 | Utsugida | A61M 39/28 | |

* cited by examiner

SYSTEM AND METHOD FOR DETECTING AIR EMBOLISMS IN LINES FOR HEMODYNAMIC MONITORING

CROSS-REFERENCE TO RELATED APPLICATIONS

This application claims priority to U.S. Provisional Patent Application No. 62/522,798, filed Jun. 21, 2017, entitled "ARTERIAL LINE, PULMONARY ARTERY LINE AND CENTRAL VENOUS PRESSURE MONITORING LINE AIR SENSOR SYSTEM," which is herein incorporated by reference.

FIELD OF THE INVENTION

The present invention generally relates to air embolisms, and more particularly to detecting air embolisms in lines for hemodynamic monitoring.

BACKGROUND

Air embolisms are a known problem. In fact, if air embolisms occur, or are introduced, into the body, they can be deadly. As such, many prior art systems exist for detecting air embolisms. However, such systems for detecting air embolisms have been restricted to venous lines as venous systems that detect air emboli used to deliver medications at a specific rate (mL/hr). In contrast, systems for detecting air embolisms for monitoring hemodynamics for arterial, pulmonary artery, and central venous pressure monitoring lines do not exist. As such, there is a need for addressing these and/or other issues associated with the prior art.

SUMMARY

A system and method are provided for detecting air embolisms in lines for hemodynamic monitoring. In use, using a first sensor, one or more gas bubbles are detected within a first line for hemodynamic monitoring. In response to the detecting, a first clamp attached to the first line for hemodynamic monitoring is contracted.

In a first embodiment, the line for hemodynamic monitoring includes at least one of an arterial line, a pulmonary artery line, or a central venous pressure monitoring line. Additionally, the line for hemodynamic monitoring includes a swan ganz catheter, and the swan ganz catheter may include three lines comprising an arterial line, a central venous pressure line, and a pulmonary artery line.

In a second embodiment (which may be combined with the first embodiment), the first sensor may be a stand-alone sensor, or may be integrated into another device. Additionally, the first sensor may include at least one electronic chip or at least one electronic chip may be used to control the first sensor and at least one additional sensor. Further, the first sensor may include a first alarm and/or may trigger a first remote alarm In a third embodiment (which may be combined with the first or second embodiment), the detection may occur by at least one of light, sound, temperature, or pressure. In response to the detection, the first sensor may produce an alarm, alert, signal, or indicator.

In a fourth embodiment (which may be combined with any of the first or second or third embodiments), the first clamp may be of a variable width and may be constructed of any one of metal, plastic, rubber, glass, or a composite material. Additionally, the first line for hemodynamic monitoring may include a first transducer used to measure at least one of systolic blood pressure, diastolic blood pressure, or mean arterial pressure. Still yet, the transducer may be used to measure a blood pressure of at least one of one or more veins, a heart, or one or more arteries, and may be used to measure a blood flow or the amount of oxygen used in a blood stream. The first clamp may be located immediately before or after the first transducer. Still yet, a first pressure bag may be attached to a first end of the first line for hemodynamic monitoring, wherein the first pressure bag provides back pressure to the first line for hemodynamic monitoring

DETAILED DESCRIPTION

Figure 1:
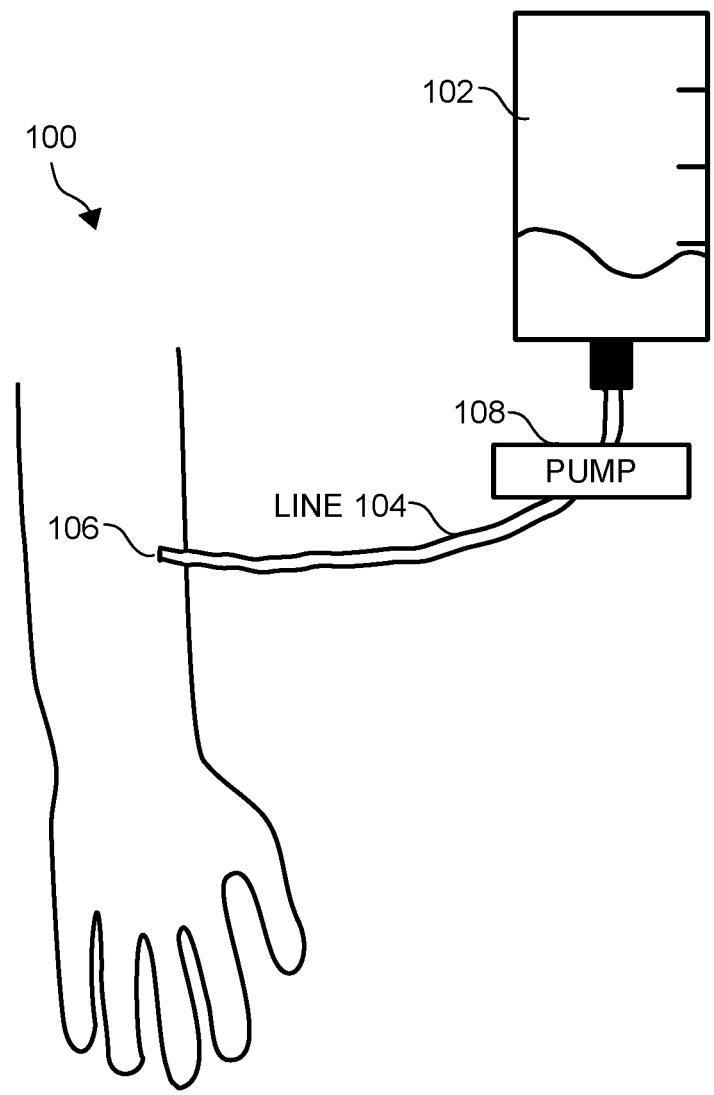
FIG. 1 illustrates an air embolism system for venous lines.

FIG. 1 illustrates an air embolism system 100 for venous lines. System 100 is an example of a representative system used for venous lines. As shown, an intravenous (IV) solution 102 is connected to an intravenous line 104. The contents of the IV solution 102 move along the IV line 104 via an IV pump 108. The IV line 104 in turn is connected to insertion point 106 where the contents of the IV solution 102 may be fed into the body of a patient. In one embodiment, an air embolism monitor system may be integrated within the IV pump 108 to detect air embolisms. For example, in one embodiment, after the contents of the IV solution 102 have been completely fed into the patient, the IV pump 108 may continue to seek to try and pump additional content (including even air) into the IV line 104. The IV pump 108 may be disabled by the air embolism monitor system to prevent air embolisms from reaching the insertion point 106. As such, the air embolism system 100 may be used in the context of administering medications (e.g. at a rate of mL/hr) and to detect and stop air embolisms with IV lines (such as IV line 104).

Figure 2:
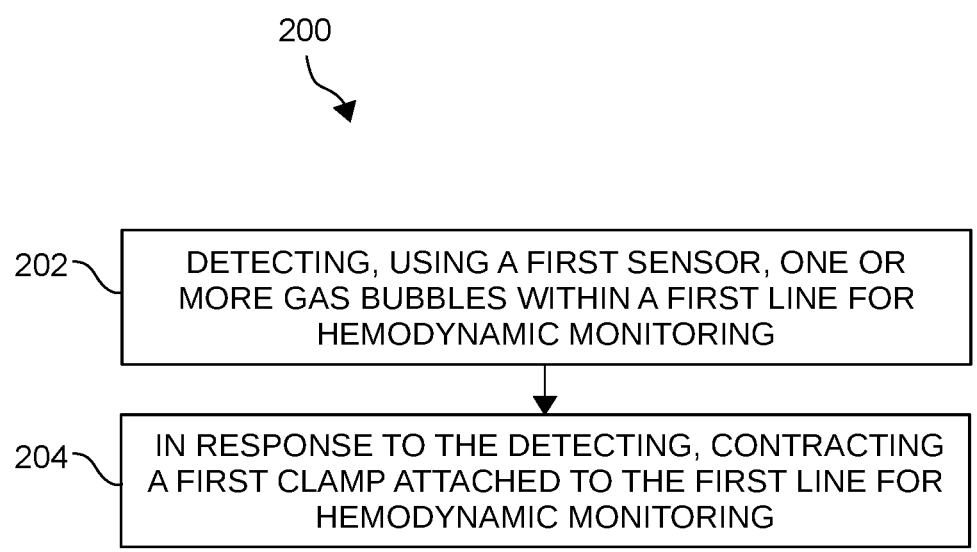
FIG. 2 illustrates a method for detecting air embolisms in lines for hemodynamic monitoring, in accordance with one possible embodiment.

In contrast, FIG. 2 illustrates a method 200 for detecting air embolisms in lines for hemodynamic monitoring, in accordance with one possible embodiment. Optionally, method 200 may be implemented in the context of any of the subsequent figures.

As shown, at operation 202, using a first sensor, one or more gas bubbles are detected within a first line for hemodynamic monitoring. In the context of the present description, a line for hemodynamic monitoring includes any of an arterial line, a pulmonary artery line, a central venous pressure monitoring line, and/or any line which may be used for hemodynamic monitoring. The line for hemodynamic monitoring may be exclusively for monitoring hemodynamics in a critical patient. For example, the line for hemodynamic monitoring may be used to measure a blood pressure inside the veins, heart, and/or arteries. Additionally, it may be used to measure blood flow and the amount of oxygen found in the blood stream of the critical patient. Still yet, lines for hemodynamic monitoring may be used to determine a condition of a critically ill patient.

Figure 6:
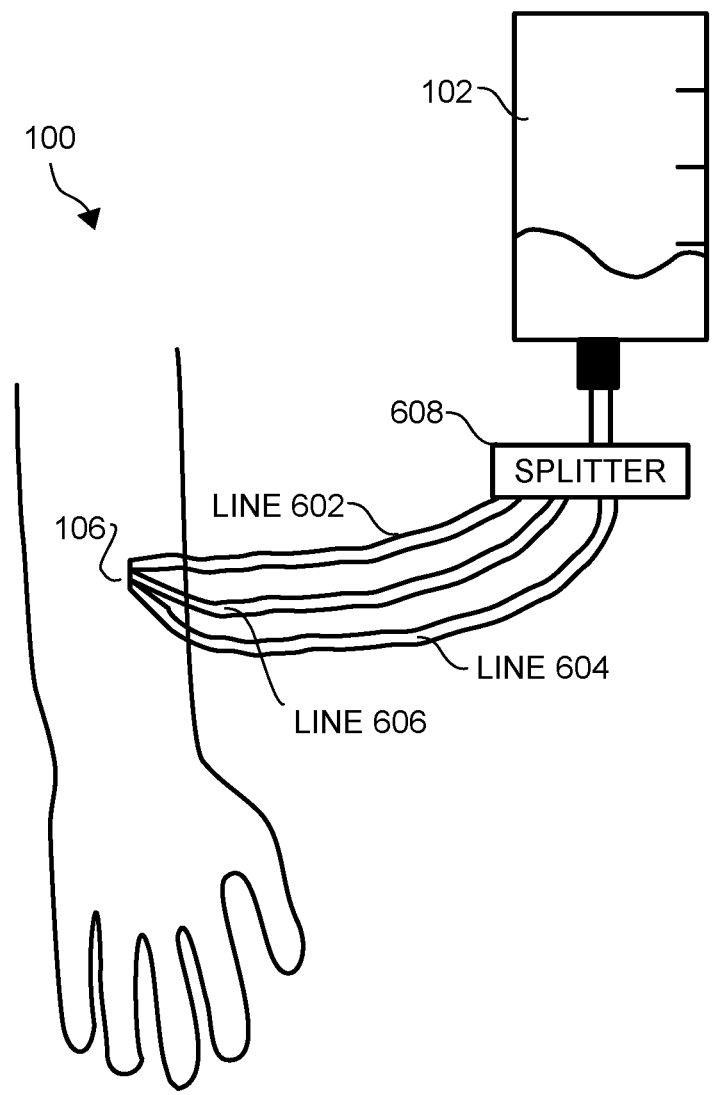
FIG. 6 illustrates an air embolism system involving a swan ganz catheter.

In another embodiment, a line for hemodynamic monitoring may include a swan ganz catheter which may be comprised of an arterial line, a central venous pressure line, and a pulmonary artery line (shown in FIG. 6 with lines 602, 604, and 606). For example, a single line (such as a first line for hemodynamic monitoring) may be attached to a pressure bag at one end, and the other end may be attached to a splitter (shown in FIG. 6 as splitter 608) that distributes the content of the pressure bag to three different and separate hemodynamic monitoring lines, one line for each of the arterial line, a central venous pressure line, and a pulmonary artery line. Each of the separate hemodynamic monitoring lines may then be attached (either individually or collectively) to a catheter which is inserted into the body of the patient. It is to be appreciated that although reference is made to a first line for hemodynamic monitoring (as well as a first sensor, a first clamp, etc.), it is to be understood that any number of lines (or sensors, clamps, etc.) may be included as part of the method 200.

In the context of the present description, the first sensor includes any sensor capable of detecting an air embolism. Of course, it is to be appreciated that any number of sensors may be used in connection to method 200. Additionally, the sensors may be located at any location along the first line for hemodynamic monitoring. Further, the first sensor may be a stand alone sensor (e.g. independent of another device), or may be integrated into another device. For example, the first sensor may be part of the first transducer, the first pressure bag, the first line for hemodynamic monitoring tubing or attached to the first insertion point into the human being or animal. Additionally, the first sensor may be connected to a computer or other electronic device.

Next, at operation 204, in response to the detecting, a first clamp attached to the first line for hemodynamic monitoring is contracted. The detection may occur by at least one of light, sound, temperature, or pressure. Additionally, the use of light by the first sensor may include detecting wavelengths, use of infrared light, photo detection, frequency modulation, oscillation, or any other form of detection involving the use of light. The use of sound by first sensor may include the identification of a sound algorithm or pattern, breaking sound waves into minute digital slices, detecting frequency, using sonar transducers, or any other form of detection involving the use of sound. The use of temperature by the first sensor may include measurement of heat energy or coldness generated on the system, detection of a physical change to temperature that may produce an analogue or digital output, or any other form of detection involving the use of temperature. The use of pressure by the first sensor may include electronic use of force to measure strain over an area, measurement of expansion or contraction of the area, measurement of pressure relative to atmospheric pressure, measurement of pressure between two different areas, and/or any other form of detection involving the use of pressure. Further, the first sensor may detect using any combination of light, sound, temperature, or pressure.

With respect to the first sensor, the first sensor may include at least one electronic chip. Additionally, in the context of the present description, the chip may be an integrated circuit (e.g. analog, digital, or mixed signal), a programmable chip(s), and/or any other form of electronic chip. Further, the at least one electronic chip may be used to control the first sensor and at least one additional sensor, and/or any number of sensors. Still yet, the first sensor may produce an alarm, alert, signal, or indicator in response to the detection. For example, if the first sensor detects gas bubbles within the line for hemodynamic monitoring, an audible alarm may be produced by the first sensor. In this manner, the first sensor may include a first alarm. In another embodiment, the first sensor may trigger a first (or any number of) remote alarm. The first alarm may include a bell, buzzer, and/or vibration that provides feedback.

In one embodiment, the first clamp may be of variable widths. For example, the first clamp may be configured to be adapted to a first width, and/or any number of predetermined widths. Additionally, the first clamp may be constructed of any one of metal, plastic, rubber, glass, or a composite material. Further, the first clamp may be constructed of material that is safe for use with a magnetic resonance imaging (MRI) system.

In another embodiment, the first line for hemodynamic monitoring may include a first transducer used to measure at least one of systolic blood pressure, diastolic blood pressure, or mean arterial pressure. Additionally, the first clamp may be located on the first line for hemodynamic monitoring immediately before or immediately after the first transducer. Of course, the first clamp may be located at any position along the first line for hemodynamic monitoring.

Still yet, in one embodiment, the first line for hemodynamic monitoring may be connected to a first pressure bag which may provide back pressure to the first line for hemodynamic monitoring.

The following description of the embodiment(s) is merely exemplary (illustrative) in nature and is in no way intended to limit the invention, its application, or uses. Additionally, the invention may be practiced according to the claims without some or all of the illustrative information.

Figure 3:
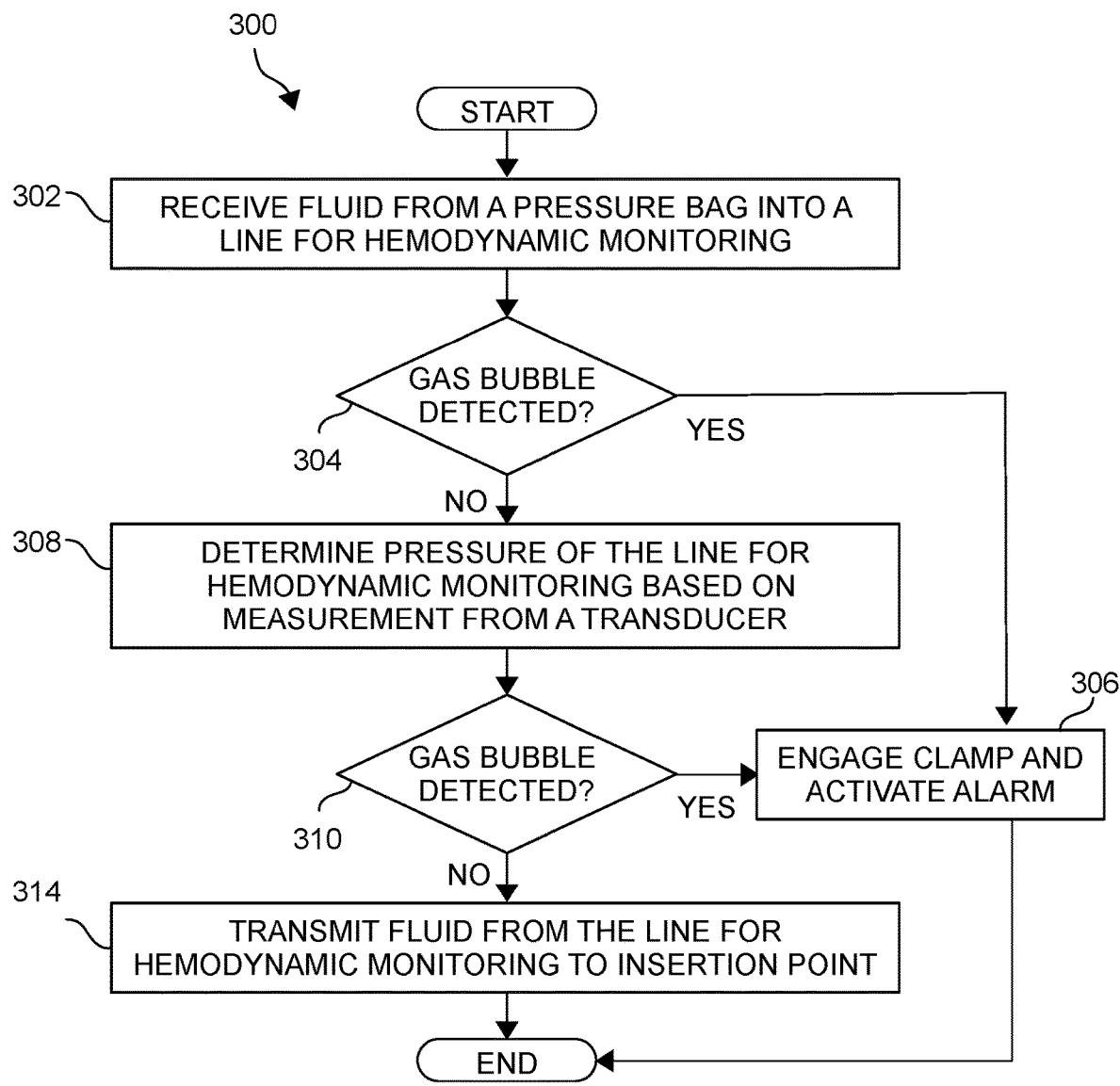
FIG. 3 illustrates a method for detecting air embolisms in lines for hemodynamic monitoring, in accordance with one possible embodiment.

FIG. 3 illustrates a method 300 for detecting air embolisms in lines for hemodynamic monitoring, in accordance with one possible embodiment. Optionally, method 300 may be implemented in the context of any of FIG. 2 and/or subsequent figures.

As shown, at operation 302, fluid is received from a pressure bag into a line for hemodynamic monitoring. Next, at decision 304, it is determined whether gas bubbles are detected. If gas bubbles are detected, then at operation 306, a clamp is engaged and an alarm is activated and the method ends.

If no gas bubbles are detected (per decision 304), then at operation 308, pressure of the line for hemodynamic monitoring is determined based on a measurement from a transducer. Next, at decision 310, it is determined whether gas bubbles are detected. If gas bubbles are detected, then at operation 306, a clamp is engaged and an alarm is activated and the method ends.

At operation 314, if gas bubbles are not detected, fluid is transmitted from the line for hemodynamic monitoring to the insertion point (e.g. within a human, animal, etc.), and the method 300 ends. In one embodiment, the purpose of the fluid being transmitted from the line for hemodynamic monitoring (per operation 314) may including the ability to then measure a blood pressure inside the veins, heart, and arteries, measure blood flow and the amount of oxygen found in the blood stream of the critical patient. In this manner, the lines for hemodynamic monitoring may be used to determine a condition of a critically ill patient.

In one embodiment, after transmitting fluid from the line for hemodynamic monitoring to the insertion point (per operation 314), the method 300 may repeat back to operation 302 and continue to receive additional fluid in the arterial. In this manner, fluid within the line for hemodynamic monitoring is continually and constantly monitored to detect the presence of any gas bubbles.

Figure 4:
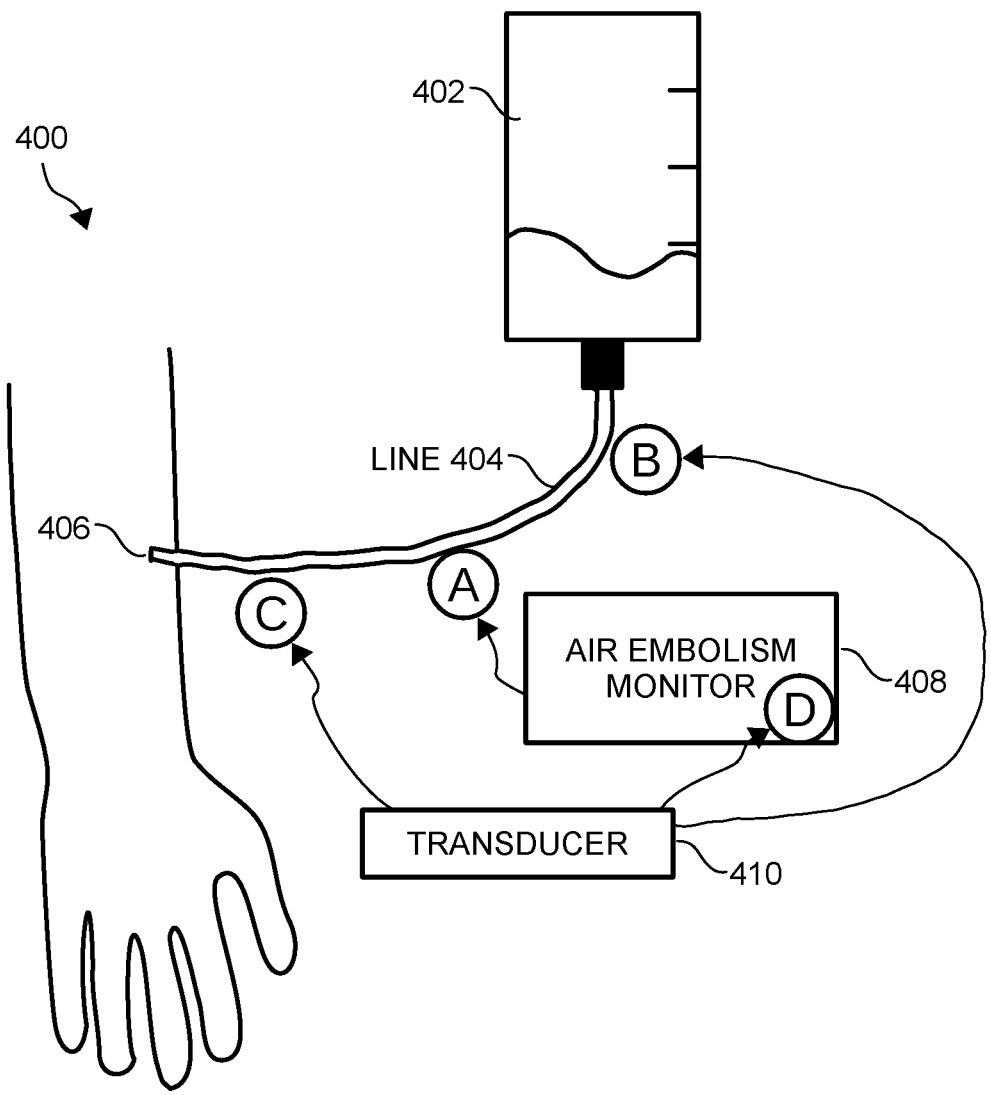
FIG. 4 illustrates a line for hemodynamic monitoring in an air embolism system, in accordance with one embodiment.

FIG. 4 illustrates a line for hemodynamic monitoring air embolism system 400, in accordance with one possible embodiment. Optionally, the system 400 may be implemented in the context of any of FIGS. 1-2, and/or subsequent figures.

As shown, the system 400 depicts a first pressure bag 402, a first line for hemodynamic monitoring 404, a first insertion point 406, an air embolism monitor 408, and a first transducer 410. The air embolism monitor 408 may be located at point "A" on the line for hemodynamic monitoring 404.

Additionally, the first transducer 410 may be located at a variety of locations, including before the air embolism monitor "B", after the air embolism monitor "C", and/or as part of the air embolism monitor "D". In one embodiment, more than one transducer may be included within system 400. As such, a transducer may be located both before, within, and after the air embolism monitor 408. In one embodiment, the first transducer 410 may measure the systolic blood pressure, diastolic blood pressure, or mean arterial pressure of the human being or animal.

In one embodiment, the air embolism monitor 408 may include a first sensor (or any number of sensors) used for detection of one or more gas bubbles in the first line for hemodynamic monitoring 404.

Figure 5:
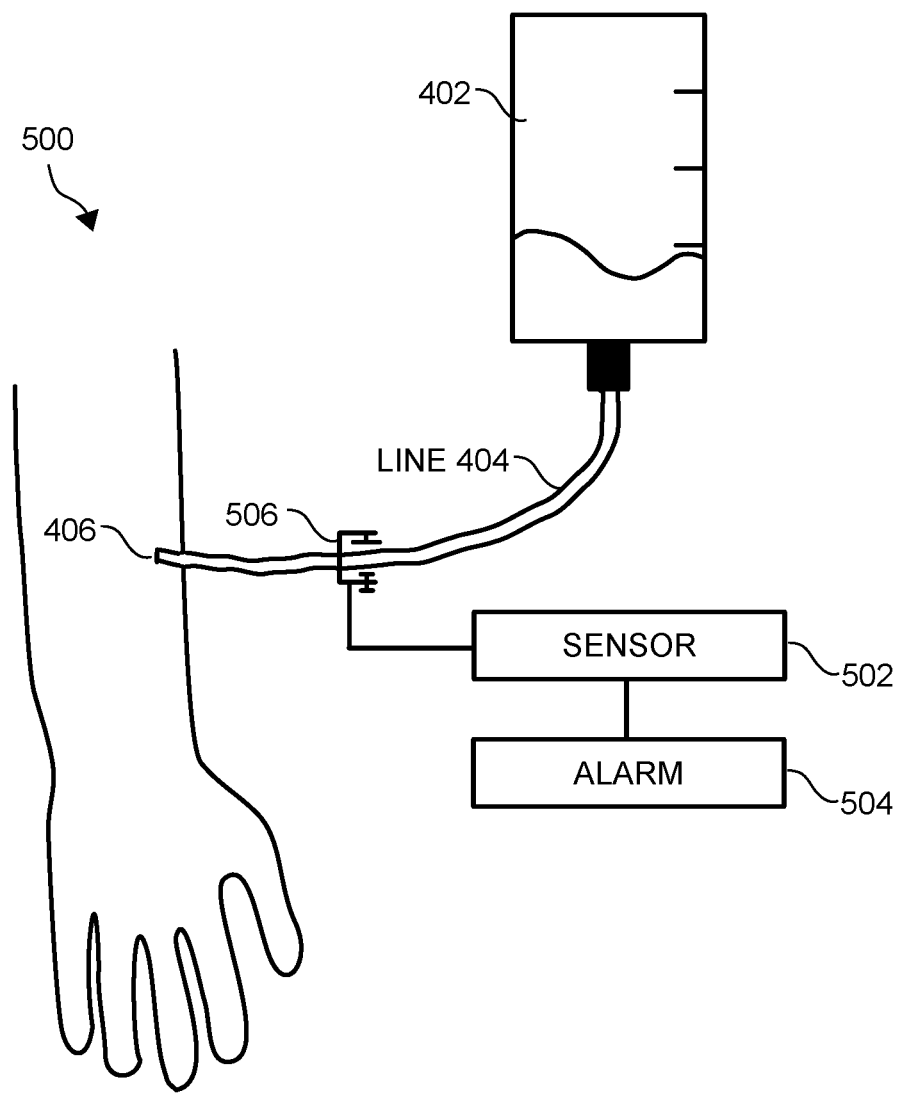
FIG. 5 illustrates a line for hemodynamic monitoring in an air embolism system, in accordance with one possible embodiment.

FIG. 5 illustrates a line for hemodynamic monitoring air embolism system 500, in accordance with one possible embodiment. Optionally, the system 500 may be implemented in the context of any of FIGS. 2-4.

As shown, the system 500 depicts the first pressure bag 402, the first line for hemodynamic monitoring 404, the first insertion point 406, a first sensor 502, a first alarm 504, and a first clamp 506. The system 500 shows an alternative arrangement building upon the components of FIG. 4. As such, the prior components (including for example transducer 410) are included as being part of FIG. 5.

The first sensor 502 may be located at a first clamp 506 or before or after or both. In one embodiment, a first clamp 506 may prevent movement of fluid or one or more gas bubbles or both in the first line for hemodynamic monitoring 404. In another embodiment, a first clamp 506 may be located in multiple locations on the first line for hemodynamic monitoring 404. Additionally, the first clamp 506 may be constructed of any one of metal, plastic, rubber, glass, or a composite material.

The first sensor 502 may be included with transducer 410, air embolism monitor 408, and/or may be a stand-alone device included with system 400 and/or system 500. Additionally, the alarm 504 may be integrated within the first sensor 502 and/or any of the transducer 410 or air embolism monitor 408. In this manner, when the first sensor 502 detects an air embolism, both the first alarm 504 and the first clamp 506 may be activated. It is to be appreciated that any number of alarms (e.g. wireless notification, SMS text, etc.) and clamps (e.g. insertion point cut-off valve, etc.) may be activated by the sensor.

In various embodiment, the methods and systems disclosed herein may be used to avoid air embolisms. For example, in response to detecting the existence of air in a line for hemodynamic monitoring, a clamp may be applied to the line for hemodynamic monitoring (e.g. via mechanical clamp) to prevent an air embolism from entering arterial blood through a line for hemodynamic monitoring. Additionally, in response to detecting the existence of air in a line for hemodynamic monitoring, the air embolism monitor may transmit such information to the clamp such that the clamp, in turn, responds by contracting. In another embodiment, so as to cause the clamp to contract over and occlude the line. Or, the air embolism monitor may transmit information regarding the presence of air to a computer, which may then transmit instructions to the clamp to contract. In this manner, air or gas bubbles may be prevented from continuing on within the line for hemodynamic monitoring, thereby preventing damage (or potential death) of the patient.

In other embodiments, the air embolism monitor may be portable or, in another embodiment, the air embolism monitor may be secured onto a pole. For example, the pole may also hold the pressure transducer and/or any other necessary sensor or device. In one embodiment, the air embolism monitor may be located above the transducer. However, it is to be appreciated that the air embolism monitor may function above or below the transducer on the line for hemodynamic monitoring. For example, a pressure bag may run dry (e.g. it is empty), causing potentially air to be introduced into the line. The air embolism monitor, located below such pressure bag, may detect air within the line for hemodynamic monitoring, and cause the clamp to prevent any air from entering the body.

In another embodiment, the features disclosed herein may be applicable for use with magnetic resonance imaging (MRI) systems. As such, the line for hemodynamic monitoring may be composed of material (e.g. non-metal) that may operate safely with a MRI system.

While specific embodiments of the invention have been described, it is understood that the present invention is not intended to be limited only to such embodiments. Additionally, the scope of the preferred embodiment should be defined by the following claims and their equivalents. Moreover, any combination of the above-described elements in all possible variations thereof is encompassed unless otherwise indicated herein or otherwise clearly contradicted by context. Further, the use of the terms "a" and "an" and "the" and "the first" and similar references in the context of describing the subject matter (particularly in the context of the claims) are to be construed to cover both the singular and the plural, unless otherwise indicated herein or clearly contradicted by context. No language in the specification should be construed as indicating any non-claimed element as essential to the practice of the invention as claimed.

What is claimed is:

1. An apparatus, comprising:
   an external portable hemodynamic monitoring device occurring outside of a body of a patient, wherein the external portable hemodynamic monitoring device includes a line, wherein the line of the external portable hemodynamic monitoring device:
      is used to detect one or more gas bubbles, and determine a condition of the patient,
      is constructed of a material that is safe for use with magnetic resonance imaging,
      is a swan ganz catheter which includes:
         an arterial line,
         a pulmonary artery line, and
         a central venous pressure monitoring line;
   a transducer attached to the line of the external portable hemodynamic monitoring device, wherein the transducer is used to measure:
      central venous pressure,
      pulmonary artery pressure, and
      mean arterial pressure; and at least two of:
  systolic blood pressure,
  diastolic blood pressure, or
  blood flow;
a sensor that is part of a tubing of the line of the external portable hemodynamic monitoring device, wherein the sensor is used to detect the one or more gas bubbles within the line of the external portable hemodynamic monitoring device, wherein the sensor is configured to detect the one or more gas bubbles by at least one of:
  temperature, including at least one of a temperature measurement, a detection of a physical temperature change, an analog temperature output, or a digital temperature output, or
  pressure, including at least one of a measurement of strain, a measurement of expansion, a measurement of contraction, a measurement relative to atmospheric pressure, a measurement between two different areas on the line;
a clamp attached to the line of the external portable hemodynamic monitoring device and configured to contract over the line of the external portable hemodynamic monitoring device, in response to the sensor detecting the one or more gas bubbles, wherein the clamp is constructed of a material that is safe for use with magnetic resonance imaging (MRI); and
an alarm that is triggered in response to the sensor detecting the one or more gas bubbles, wherein the alarm includes a wireless notification or a SMS text message.

2. The apparatus of claim 1, wherein the sensor includes at least one electronic chip.

3. The apparatus of claim 2, wherein the at least one electronic chip is used to control the sensor and at least one additional sensor.

4. The apparatus of claim 1, wherein, in response to the detection, the sensor produces an alert, signal, or indicator.

5. The apparatus of claim 1, wherein the clamp is constructed of any one of plastic, rubber, glass, or a composite material.

6. The apparatus of claim 1, wherein the sensor includes the alarm.

7. The apparatus of claim 1, wherein the sensor triggers a remote alarm that is separate from the alarm.

8. The apparatus of claim 1, wherein the clamp is located immediately before or after the transducer.

9. The apparatus of claim 1, further comprising a pressure bag attached to an end of the line for external hemodynamic monitoring, wherein the pressure bag provides back pressure to the line for external hemodynamic monitoring.

10. The apparatus of claim 1, wherein the sensor is connected to an external computer or electronic device.

11. An apparatus, comprising:
an external portable hemodynamic monitoring device occurring outside of a body of a patient, wherein the external portable hemodynamic monitoring device includes an arterial line, a central venous pressure line, and a pulmonary artery line, where each of the arterial line, the central venous pressure line, and the pulmonary artery line are used to detect one or more gas bubbles, and determine a condition of the patient, wherein each of the arterial line, the central venous pressure line, and the pulmonary artery line is constructed of a material that is safe for use with magnetic resonance imaging;
a transducer attached to each of the arterial line, the central venous pressure line, and the central venous line;
a first sensor integrated into the arterial line of the external portable hemodynamic monitoring device, wherein the first sensor is used to detect the one or more gas bubbles within the arterial line of the external portable hemodynamic monitoring device, wherein the first sensor is configured to detect the one or more gas bubbles by at least one of temperature, or pressure;
a first clamp attached to the arterial line of the external portable hemodynamic monitoring device and configured to contract over the arterial line of the external portable hemodynamic monitoring device, in response to the first sensor detecting the one or more gas bubbles, wherein the first clamp is constructed of a material that is safe for use with magnetic resonance imaging (MRI);
a second sensor integrated into the central venous pressure line of the external portable hemodynamic monitoring device, wherein the second sensor is used to detect the one or more gas bubbles within the central venous pressure line of the external portable hemodynamic monitoring device, wherein the second sensor is configured to detect the one or more gas bubbles by at least one of temperature, or pressure;
a second clamp attached to the central venous pressure line of the external portable hemodynamic monitoring device and configured to contract over the central venous pressure line of the external portable hemodynamic monitoring device, in response to the second sensor detecting the one or more gas bubbles, wherein the second clamp is constructed of a material that is safe for use with magnetic resonance imaging (MRI);
a third sensor integrated into the central venous line of the external portable hemodynamic monitoring device, wherein the third sensor is used to detect the one or more gas bubbles within the central venous line of the external portable hemodynamic monitoring device, wherein the third sensor is configured to detect the one or more gas bubbles by at least one of temperature, or pressure;
a third clamp attached to the central venous line of the external portable hemodynamic monitoring device and configured to contract over the central venous line of the external portable hemodynamic monitoring device, in response to the third sensor detecting the one or more gas bubbles, wherein the third clamp is constructed of a material that is safe for use with magnetic resonance imaging (MRI); and
an alarm that is triggered in response to any of the first sensor, the second sensor, or the third sensor detecting the one or more gas bubbles, wherein the alarm includes a wireless notification or a SMS text message.

* * * * *